United States Patent [19]

Kordas et al.

[11] Patent Number: 5,519,323
[45] Date of Patent: May 21, 1996

[54] INTEGRABLE CONDUCTIVITY MEASURING DEVICE

[75] Inventors: Norbert Kordas, Essen; Yiannos Manoli, Mülheim, both of Germany

[73] Assignee: Fraunhofer-Gesellschaft zur Forderung der Angewandten Forschung e.v., Munich, Germany

[21] Appl. No.: 335,748

[22] PCT Filed: Feb. 17, 1993

[86] PCT No.: PCT/DE93/00170

§ 371 Date: Nov. 14, 1994

§ 102(e) Date: Nov. 14, 1994

[87] PCT Pub. No.: WO93/23758

PCT Pub. Date: Nov. 25, 1993

[30] Foreign Application Priority Data

May 15, 1992 [DE] Germany ............... 42 16 176.2

[51] Int. Cl.⁶ ............... G01N 27/06; G01R 27/22
[52] U.S. Cl. ............... 324/444; 324/449; 324/690; 257/532
[58] Field of Search ............... 324/439, 444, 324/446, 449, 715, 690, 722, 724; 330/7, 9, 10, 51; 307/110; 257/532

[56] References Cited

U.S. PATENT DOCUMENTS

| | | | |
|---|---|---|---|
| 3,495,165 | 2/1970 | Dauphinee | 324/444 |
| 3,757,205 | 9/1973 | Dauphinee | 324/444 |
| 4,010,715 | 3/1977 | Robar. | |
| 4,656,427 | 4/1987 | Dauphinee | 324/444 |
| 4,833,413 | 5/1989 | Head | 324/449 |
| 4,931,897 | 6/1990 | Tsukamoto et al. | 257/532 X |
| 4,988,952 | 1/1991 | Sevastopoulos et al. | 330/51 |
| 5,142,238 | 8/1992 | White | 330/51 X |
| 5,349,494 | 9/1994 | Ando | 257/532 X |

FOREIGN PATENT DOCUMENTS

| | | |
|---|---|---|
| 3705714 | 9/1988 | Germany. |
| 0094811 | 7/1981 | Japan. |
| 9218856 | 10/1992 | WIPO. |

*Primary Examiner*—Kenneth A. Wieder
*Assistant Examiner*—Diep Do
*Attorney, Agent, or Firm*—Wolf, Greenfield & Sacks

[57] ABSTRACT

A conductivity measuring device has a current source device connected to two current supply elements through which a substantially square-wave current can be fed into a liquid, and a measuring circuit for determining the voltage drop in the liquid between voltage measuring elements. In order to provide such an integrable conductivity measuring device which prevents polarization effects, which avoids a galvanic connection to the liquid whose conductivity is to be measured, and which permits a simple detection of the conductivity of said liquid, it is suggested that the measuring circuit should be a switch-capacitor circuit including a measuring capacitor, a differential amplifier having a feedback capacitor arranged in its feedback branch, and a switch by means of which the two connections of the measuring capacitor are connected in time dependence on the behavior of the square-wave current to the voltage electrodes in one switching state and to the two inputs of the differential amplifier in another switching state, and that the current supply elements should be implemented as current coupling capacitors.

12 Claims, 7 Drawing Sheets

INTEGRABLE CONDUCTIVITY MEASURING DEVICE

RELATED PATENT APPLICATION

Major aspects of the subject matter of this application are related to the subject matter of U.S. Ser. No. 08/119,243 pending corresponding to PCT/DE92/00242.

DESCRIPTION

The present invention refers to an integrable conductivity measuring device for measuring the electric conductivity of liquids.

For the purpose of determining the electric conductivity of a liquid, it is generally known to impress a current upon said liquid and to measure the voltage drop within said liquid, said voltage drop being inversely proportional to the conductivity of the liquid.

In the simplest case, only two electrodes are used for this purpose. The current is impressed upon the liquid via these two electrodes and, simultaneously, the voltage drop is measured by means of the same electrodes. On this occasion, so-called polarization effects occur, which distort the actual measuring signal. These effects occur whenever a current flows over a boundary layer between an electrode and an electrolyte. In view of the act that a flow of current in an electrolyte entails ion migration, ions of one type of charge will accumulate at the boundary layer between the electrolyte and the electrode, said ion accumulations weakening the original field and reducing the measuring signal.

In order to avoid this disadvantage, conductivity measuring devices with a socalled four-electrode arrangement are used, wherein a current source with two current electrodes is provided for impressing a measuring current. Two further electrodes, which can be referred to as voltage electrodes, serve to measure the voltage dropping across the liquid. The voltage drop, which is tapped by the voltage electrodes, is amplified by a high-ohmic amplifier connected downstream of said voltage electrodes. On account of the high input impedance of the amplifiers, the current flowing via the voltage electrodes can be kept small so that the polarization effects will be reduced when this measuring method is used, and this will result in an improved measuring accuracy in comparison with conductivity measurements making use of only two electrodes. However, also in the four-electrode arrangement the measuring current flowing via the voltage electrodes will cause a polarization and, consequently, a distortion of the measuring signal.

U.S. Pat. No. 4,656,427 already discloses a conductivity measuring device of the type mentioned at the beginning, which works with a four-electrode arrangement. Two current electrodes are adapted to be acted upon by a square-wave current. Two voltage electrodes, which are followed by capacitors for separating dc potentials, serve to detect the dynamic change in potential caused by the square-wave alternating current impressed upon the liquid to be measured. This signal is amplified by a subsequent evaluation circuit, which is provided with an additional capacitor connected in series and used for separating offset currents, and, after an analog-to-digital conversion, it is displayed on a display unit.

In conductivity measuring devices of the type described hereinbefore, it is also known to produce the impressed current as a sinusoidal alternating current so as to prevent by means of this measure decomposition processes in the liquid, which would occur if the measurement were carried out with an impressed direct current.

In order to eliminate these problems of the known integrable conductivity measuring devices comprising two voltage electrodes and two current electrodes, the prior, not-prepublished PCT/DE92/00242 (WO 92/18856) corresponding to U.S. Ser. No. 08/119,243 suggests that the current source device should produce a square-wave current which is supplied to the two current electrodes, and that the measuring circuit should be implemented as a switch-capacitor circuit provided with a measuring capacitor which is adapted to be coupled to and separated from the voltage electrodes via a switch means in time-dependence on the behaviour of the substantially square-wave current.

The measuring errors occurring due to polarization effects in the prepublished prior art are completely avoided with the aid of the subject matter of PCT/DE92/00242 (WO 92/18856).

The impression of the current upon the liquid (the electrolyte) as well as the measurement of the voltage are carried out via a direct galvanic contact between the conductivity measuring device and the electrolyte. For this purpose, electrodes are used, which consist of precious metals, steel or carbon and which are referred to as socalled "Kohlrausch" cells. The galvanic contact results, however, in undesired electrochemical effects at the boundary layer between the electrodes and the electrolyte.

These effects are, among others, the following ones:

Additional voltage drops, primarily when a current flows, which have to be compensated for in the measurement procedure.

Electrolysis processes, i.e. discharges and depositions of ions on the electrodes.

Absorption of ions and contamination of the electrodes, which may cause drift errors.

In the case of malfunction, a direct-current path through the electrolyte exists, and this direct-current path may cause an electrolysis of the electrolyte. In specific cases of use, e.g. in the field of invasive medical diagnostics, this will have to be compensated for by additional measures in the field of circuit technology.

Due to the galvanic coupling, the electrolyte is at a fixed potential, and this is undesirable in connection with specific cases of use.

The presence of a metal or of some other conductive material may cause undesirable chemical reactions, one of these reactions being, for example, the catalytic effect of platinum.

In order to avoid the above-mentioned effects, contactless measurement methods for determining the conductivity of liquids have already been developed. In connection with these measurement methods, a distinction has to be made between two principles: one of said methods works with inductive coupling between a measuring circuit and the electrolyte, whereas the other method uses capacitive coupling.

The inductive method comprises e.g. the feature that the electrolyte, which has been introduced in a closed tube, effects coupling of otherwise separated windings of a transformer. A primary winding has applied thereto an alternating voltage, which will cause a flow of current in the electrolyte. This flow of current generates in a secondary winding a voltage whose value depends on the conductivity of the electrolyte. The expenditure for the apparatuses required for this method is, however, very high.

A capacitive coupling in accordance with the other one of the above-mentioned measurement methods is achieved by constructing part of the walls of the vessel containing the electrolyte as capacitors. Part of such a capacitor is formed by a metallic layer which is covered by a thin layer of glass. The respective counterelectrode is formed by the electrolyte. The electric equivalent circuit diagram of such an arrangement consists of two capacitors of this type and the ohmic electrolyte resistor between said capacitors. In the known capacitive measurement methods, these elements are introduced in a high-frequency oscillating circuit in which the electrolyte resistor determines e.g. the attenuation behaviour which is evaluated subsequently. Just as in the case of the inductive method, the expenditure for the apparatuses required is again very high. In view of the fact that the capacitances which can be achieved are only small, the capacitive method additionally necessitates a high measuring frequency. Furthermore, a simple linear relationship between the conductivity and the measured quantity does not exist.

It is a major object of the present invention to provide an integrable conductivity measuring device which prevents polarization effects, which avoids a galvanic connection to the liquid whose conductivity is to be measured, and which permits a simple detection of the conductivity of said liquid.

This object is achieved by an integrable conductivity measuring device for measuring the electric conductivity of liquids, comprising a current source device adapted to be connected to two current supply elements through which a substantially square-wave current can be fed into the liquid, and a measuring circuit connected to two voltage measuring elements and used for determining the voltage drop in the liquid between said voltage measuring elements, said voltage drop depending on the electric conductivity of the liquid examined, wherein the measuring circuit is a switch-capacitor circuit including a measuring capacitor, a differential amplifier having a feedback capacitor arranged in its feedback branch, and a switch means with the aid of which the two connections of the measuring capacitor are connected in time dependence on the behaviour of the square-wave current to the voltage electrodes in one switching state and to the two inputs of the differential amplifier in another switching state, and the current supply elements are implemented as current coupling capacitors.

In short, the integrable conductivity measuring device according to the present application differs from the subject matter of the prior, not-prepublished PCT/DE92/00242 (WO 92/18856) corresponding to U.S. Ser. No. 08/119,243 with regard to the fact that at least the current supply elements, which are implemented as current electrodes in accordance with PCT/DE92/00242 (WO 92/18856) corresponding to U.S. Ser. No. 08/119,243, are implemented as current coupling capacitors along the lines of the present invention. In accordance with an essential aspect of the present invention, also the voltage measuring elements are implemented as voltage decoupling capacitors so that a complete galvanic separation is achieved between the conductivity measuring device and the liquid whose conductivity is to be measured.

The conductivity measuring device according to the present invention is based on a purely capacitive coupling between the conductivity measuring device and the liquid or electrolyte, the coupling capacitors being preferably integrated-technology elements, which have a thin insulating layer on top of a conductive layer. The counterelectrode is respectively formed by the liquid or electrolyte. The resultant capacitors can be produced in a size which is sufficiently large to permit a constant current to flow via two capacitors, which serve as current supply elements, for a specific period of time. Also the resulant voltage drop in the liquid is constant for this period of time and can be detected and further processed with the aid of two voltage measuring elements, which are implemented as voltage decoupling capacitors and which are preferably arranged between the two current coupling capacitors.

Due to the galvanic separation, the formation of a direct-current path through the electrolyte or the liquid can be prevented when the conductivity measuring device according to the present invention is used. Furthermore, the application of a fixed potential to the liquid is prevented. This permits the conductivity measuring device according to the present invention to be used in areas with high safety requirements.

The measuring circuit is adapted to be monolithically integrated on a semiconductor substrate with all components. The small size of the integrable conductivity measuring device according to the present invention permits the use in connection with small sample volumes or at other points which are difficult to get at.

In the following, embodiments of the integrable conductivity measuring device according to PCT/DE92/00242 as well as according to the present invention will be explained in detail with reference to the drawings enclosed, in which

FIG. 5b shows the electric equivalent circuit diagram of the arrangement of the coupling capacitors according to FIG. 5a;

FIG. 6c is a collection of waveforms showing, as a function of time, the voltages at points A–D, respectively, within the equivalent circuit diagram of FIG. 6a;

Figure 1:
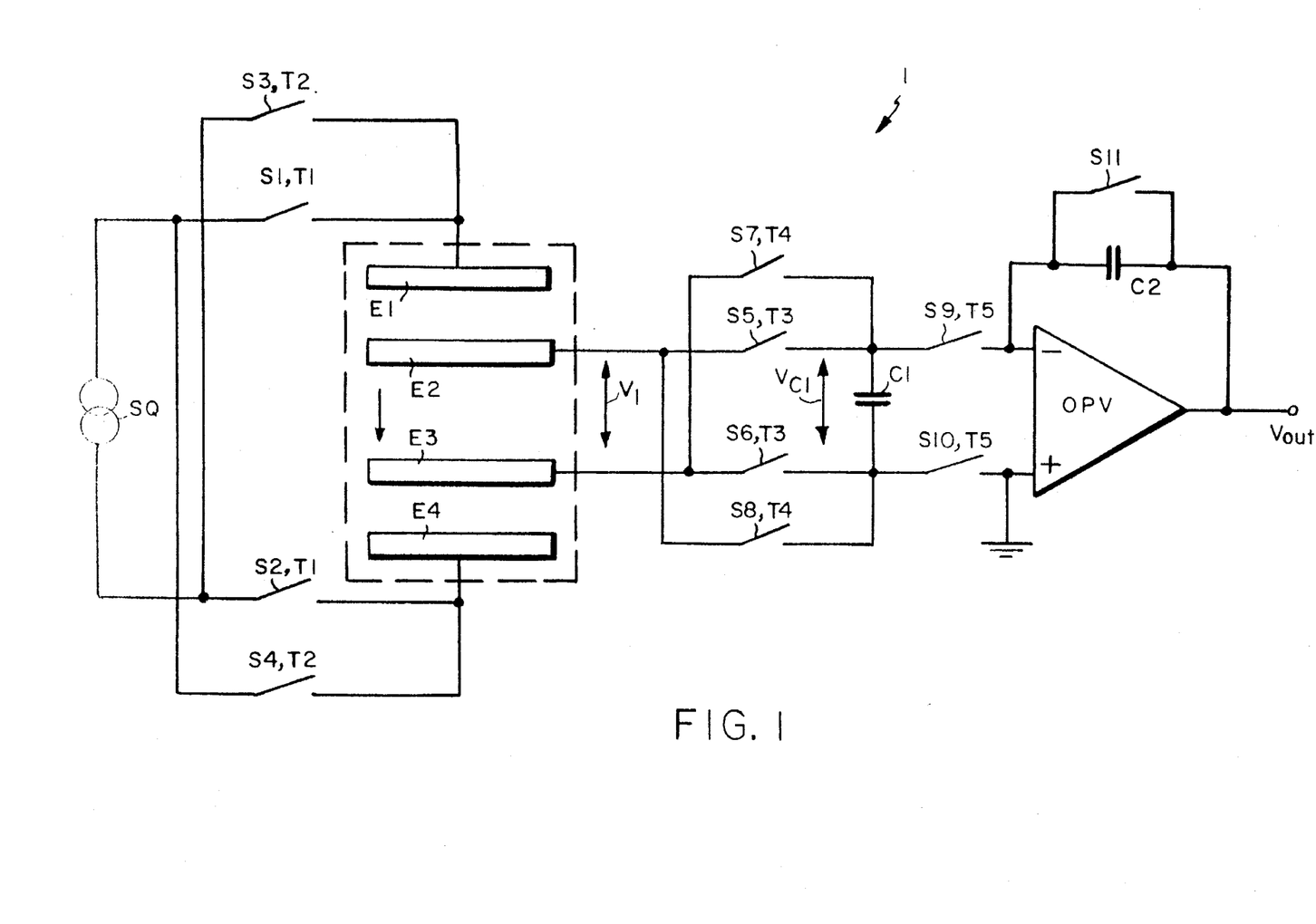
FIG. 1 shows a circuit diagram of the conductivity measuring device.

The preferred embodiment of the integrable conductivity measuring device, which is shown in FIG. 1 and which is generally designated by reference numeral 1, includes a current source SQ, which is used for producing an impressed direct current and which is adapted to be connected to two current electrodes E1, E4 in a first polarity or in a polarity opposite to said first polarity via first to fourth switches S1, S2, S3, S4 in dependence on the switching condition of said switches.

The current electrodes produce in an electrolyte EL a square-wave current without any dc component.

A control device (not shown) controls the first to fourth switches S1 to S4 in such a way that the current source SQ is connected to the current electrodes E1, E4 alternately during a first period of time T1 in the first polarity and during a second period of time T2 in the second polarity. The first and second periods of time T1, T2 have the same lengths.

Two voltage electrodes E2, E3 are arranged between the current electrodes E1, E4 in the electrolyte EL, said voltage electrodes measuring the voltage drop V1 across the electrolyte due to the impressed square-wave current between the current electrodes E1, E4.

Figure 2:
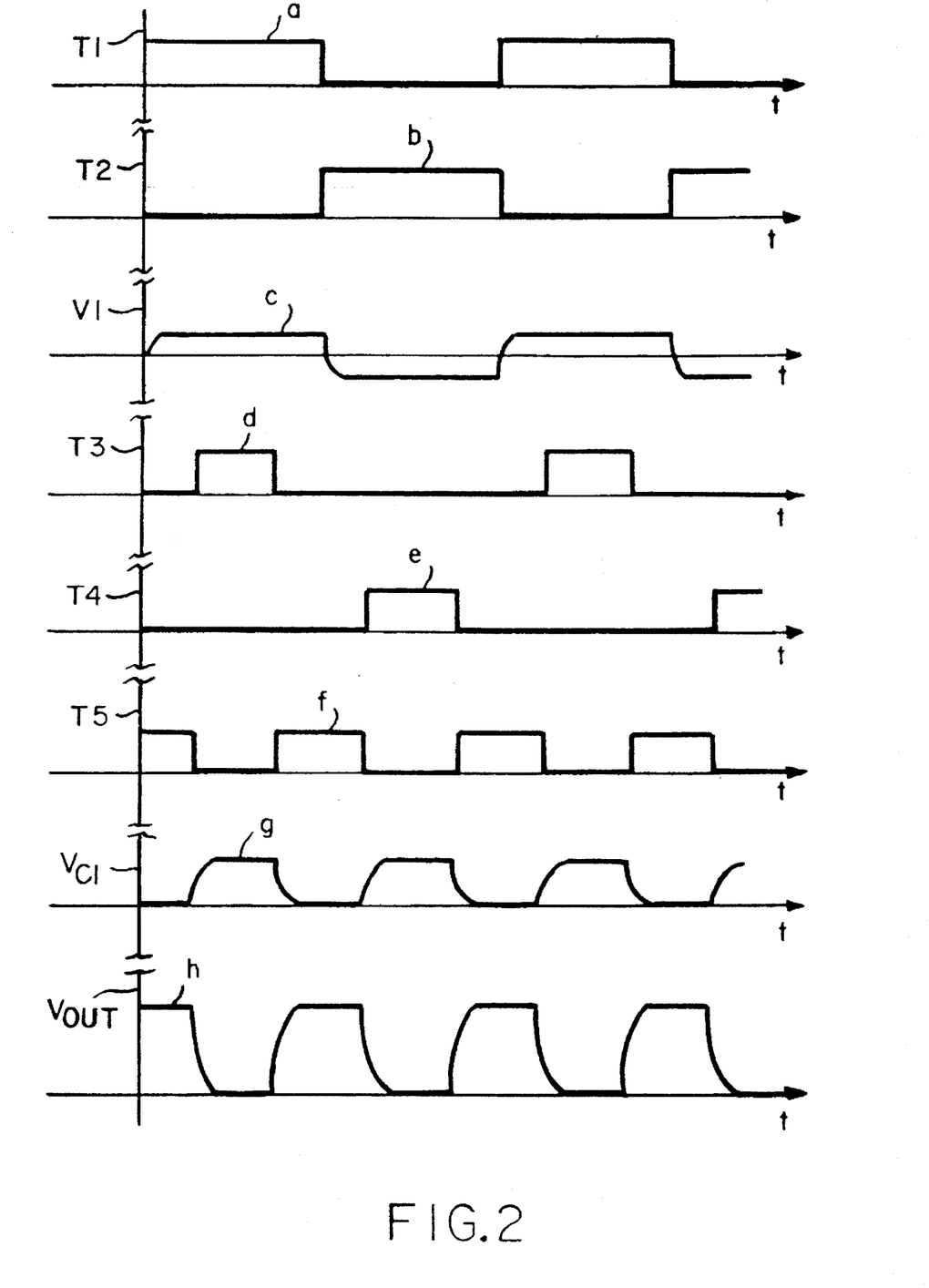
FIG. 2 shows a time chart of currents and voltages occurring in the conductivity measuring device according to FIG. 1.

The variation with time of the voltage drop V1 with reference to the first and second periods of time T1, T2 is shown in FIG. 2, waveforms a–c.

The voltage electrodes E2, E3 are adapted to be connected to the electrodes of a measuring capacitor C1 via fifth to eighth switches S5, S6, S7, S8 in a first or second polarity.

The fifth, sixth, seventh and eighth switches S5 to S8 are also controlled by the control device (not shown) which can be implemented as a microprocessor. The control is effected such that the voltage electrodes E2, E3 are connected to the measuring capacitor C1 during a third period of time T3 in the first polarity and during a fourth period of time T4 in the second polarity. As can be seen from waveforms d and e of FIG. 2 with respect to waveforms a and b of FIG. 2, the third period of time T3 lies within the first period of time T1 and the fourth period of time T4 lies within the second period of time T2.

Ninth and tenth switches S9, S10 lie between the two electrodes of the measuring capacitor C1 and the inverting or non-inverting input of an operational amplifier OPV whose output is connected to the inverted input thereof via a feedback capacitor C2.

The control device (not shown) connects the measuring capacitor C1 to the inputs of the operational amplifier OPV during a respective fifth period of time lying not within said third and fourth periods of time T3, T4. According to the capacitance relationship between the feedback capacitor C2 and the measuring capacitor C1, the voltage across the measuring capacitor $V_{C1}$ will thus be amplified to a voltage $V_{OUT}$ produced at the output of the operational amplifier.

In the embodiment shown, the control device (not shown) closes at the end of each fifth period of time an eleventh switch S11, which is connected in parallel with the feedback capacitor C2, so that the switch-capacitor circuit S5 to S11, C1, C2, OPV shown will work as an amplifier circuit. It is, however, also possible to close said eleventh switch S11 whenever several periods of time T1, T2 have elapsed so that the switch-capacitor circuit will work as an integrating circuit in this case.

As can be seen from the curve representing the voltage drop across the voltage electrodes E2, E3 according to waveform c of FIG. 2, the first and second periods of time have each been selected sufficiently long for change-over effects to decay and for the voltage V1 to assume an essentially constant value. Only after the decay of the change-over processes, the measuring capacitor is connected to the voltage electrodes during the time period T3. This has the effect that charge carriers flow across the voltage electrodes E2, E3 onto the electrodes of the measuring capacitor C1. At the beginning of this time period T3, this flow of current leads to a disturbance of the original field between the current electrodes E1, E4 and to a momentary polarization. As the charge of the measuring capacitor C1 increases, the measuring current at the voltage electrodes E2, E3 tends exponentially towards zero so that the voltage electrodes E2, E3 will become current-free when the time period T3 is sufficiently long. In a sufficiently long third period of time T3, which depends on the the individual case, but which can easily be determined in an experiment, the polarization effects no longer have any negative influence on the measuring accuracy which can be achieved.

The conductivity measuring device is suited for an integration of the electrodes E1 to E4, the current source circuit SQ and the amplifying electronic system including the switch-capacitor circuit on a single semiconductor substrate. By means of the monolithic integration on a semiconductor substrate, the conductivity measuring device can be miniaturized to a high degree so that measurements can be carried out in small sample volumes or at other points which are difficult to get at, as for example in the field of invasive medical diagnostics.

The circuit components can be implemented in CMOS technology. In this case, the production of the electrodes can be carried out such that it is compatible with the CMOS process, since merely the additional process step of applying a precious metal layer for the electrodes is required.

Although the conductivity measuring device is preferably suited for complete integration, also measuring circuits with separately arranged electrodes can be realized on the basis of the concept described.

The integrable conductivity measuring device according to the present invention differs from the conductivity measuring device which has been described with reference to FIG. 1 essentially with regard to the fact that the electrodes E1 to E4 of said last-mentioned conductivity measuring device have been replaced by coupling capacitors CK1, CK2, CK3, CK4. As for the rest, the circuit diagram of FIG. 4 corresponds identically to that shown in FIG. 1 so that a renewed description of the circuit arrangement can be dispensed with. Only for the sake of completeness, reference is made to the fact that the measuring capacitor is here designated by the reference sign CM, whereas the feedback capacitor is designated by the reference sign CR.

Figure 3A:
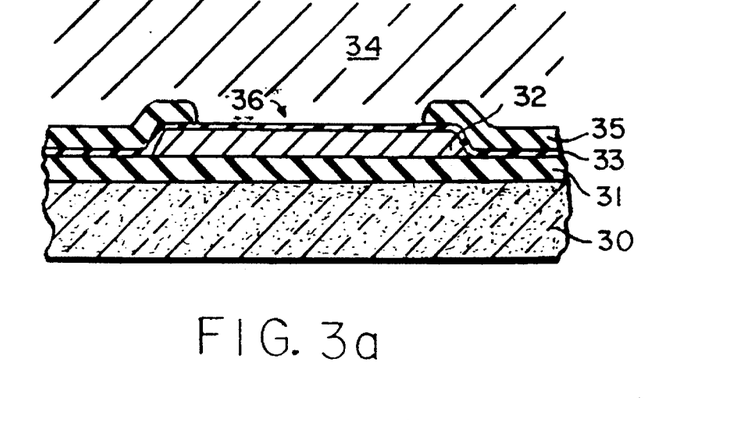
FIG. 3a shows a cross-sectional view of a coupling capacitor of the conductivity measuring device according to the present invention.

The coupling capacitors can be formed together with the conductivity measuring device such that they are integrated therein and they have preferably the structure which will be described hereinbelow with reference to FIG. 3a, 3b.

A semiconductor substrate 30 has provided thereon a conductive layer which consists preferably of polysilicon 32, said conductive layer being arranged on top of an oxide layer 31, which is a silicon oxide layer 31 in cases in which a silicon substrate is used. This polysilicon layer 32 forms one side of the coupling capacitor. A thin insulating layer 33 consisting of silicon oxide and silicon nitride is provided on said polysilicon layer 32, said insulating layer 33 separating the circuit and the poly-terminal galvanically from the electrolyte 34. The counterelectrode of this capacitor is formed by the electrolyte 34 itself, which is in direct contact with the insulating layer 33. The surface of the arrangement is covered by a protective oxide layer 35 having an opening 37 in the area of the capacitor surface 36.

Figure 3B:
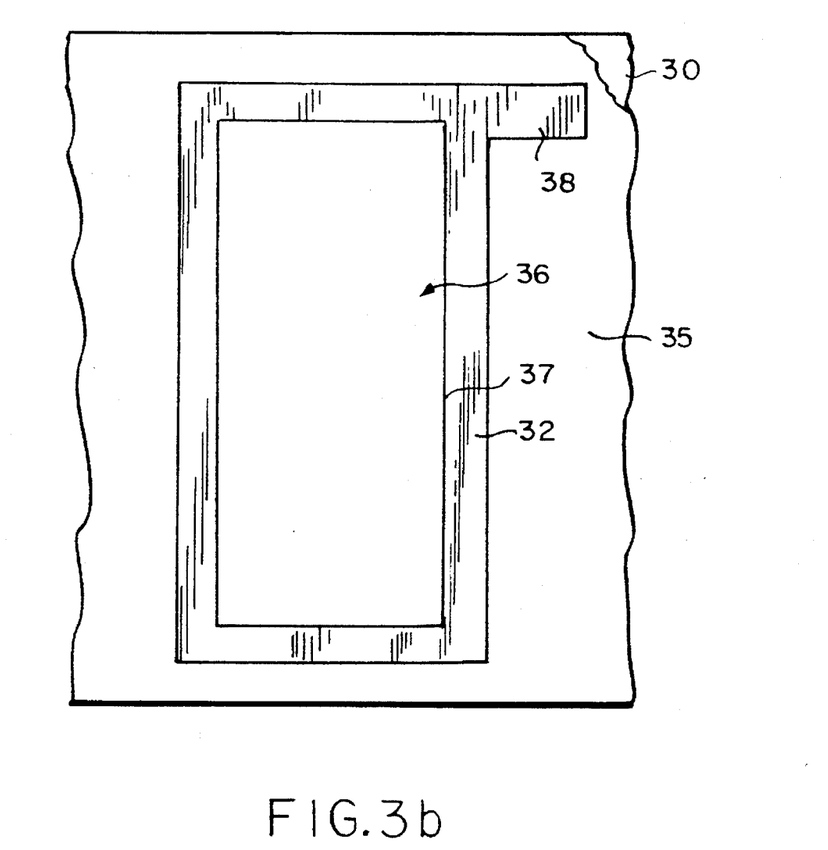
FIG. 3b shows a top view of the coupling capacitor according to FIG. 3a wherein layers other than layer 32 are treated as transparent or semi-transparent in order to show lateral placement of the layers.

As can additionally be seen in FIG. 3b, the conductive polysilicon layer 32 extends up to an extension 38 used for connection to the rest of the circuit.

The effective width of the capacitor thus formed is the thickness of the insulating layer 33. The resultant component acts as a capacitor, although only one of its sides exists in the conventional, solid form and consists of a material in which electrons are responsible for transporting the current. The other side, however, is liquid, since it is formed by the electrolyte 34, the charge transport being here carried out by dissociated ions. In view of the fact that the decisive factor with respect to a migration of electrons within the circuit as well as of ions within the electrolyte 34 is, in the final analysis, the field strength existing at the charge carrier, and in view of the fact that this field strength continues to be effective through the insulating layer 33, a displacement current can be caused to flow through the component. In the course of this process, charge carriers with opposite signs accumulate on the capacitor plates, just as in the case of conventional capacitors. The only difference is to be seen in the fact that a negative charge of electrons will, for example, form on one side, whereas a positive charge of ions will form on the opposite side.

Figure 4:
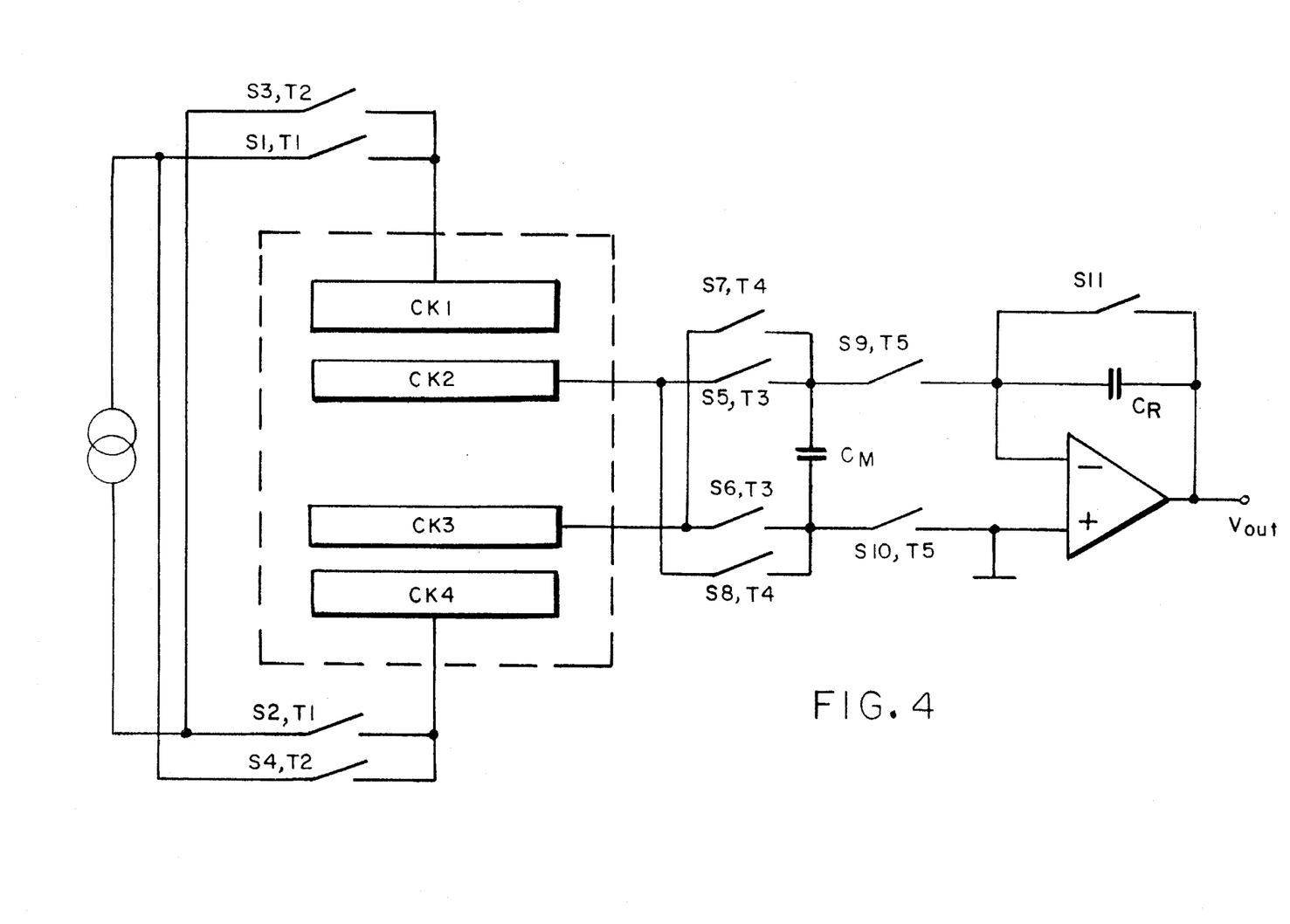
FIG. 4 shows a circuit diagram of an embodiment of the conductivity measuring device according to the present invention.
Figure 5A:
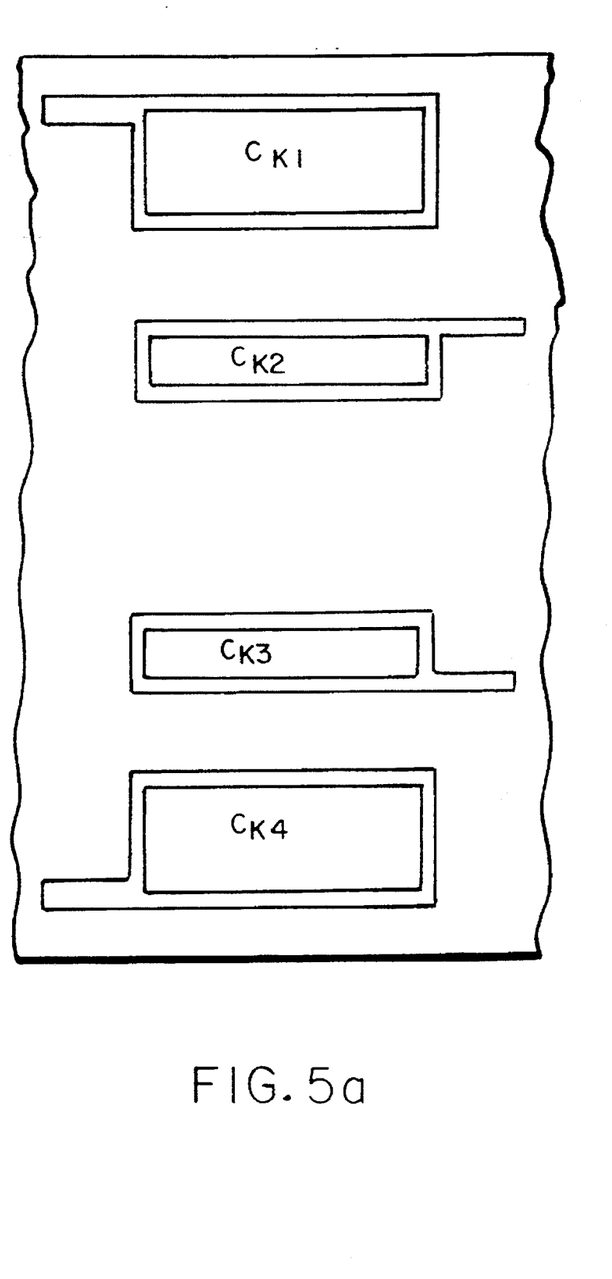
FIG. 5a shows a top view of the arrangement of the coupling capacitors of the conductivity measuring device according to FIG. 4.

As is clearly shown in FIGS. 4 and 5a, the conductivity measuring device according to the present invention comprises a total number of four coupling capacitors $C_{K1}$, $C_{K2}$, $C_{K3}$, $C_{K4}$ of this type, which are arranged on a common semiconductor substrate 30 in a planar arrangement.

In contrast to the electrodes E1 to E4, which have been used in the embodiment of FIG. 1 and which are in direct contact with the electrolyte via a conductive layer, a charge transfer between the circuit and the liquid cannot take place in the present case. In contrast to measuring cells with galvanic contact, where a direct-current path through the electrolyte exists in any case, said direct-current path causing possibly an electrolysis of the electrolyte if malfunction occurs, this disadvantageous effect is here avoided by using galvanically separated cells.

Figure 5B:
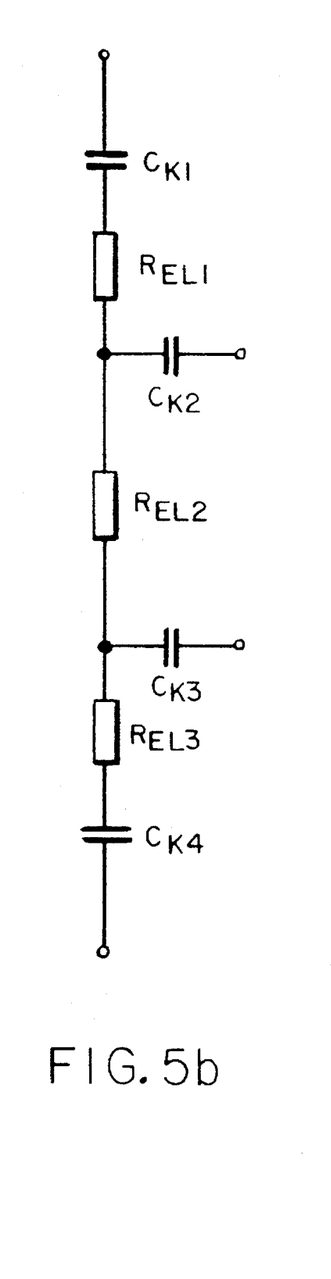

FIG. 5b shows the equivalent circuit diagram of the arrangement of the coupling capacitors according to FIG. 5a. As can be seen in said FIG. 5b, ohmic divider resistors $R_{EL1}$, $R_{EL2}$, $R_{EL3}$ lie between the coupling capacitors $C_{K1}$ to $C_{K4}$. The CMOS switches $S_5$ and $S_6$ are (in the equivalent circuit diagram according to FIG. 7a) replaced by their switch-on resistance $R_{ON}$. The switch-on resistance of these switches $S_5$, $S_6$ is only of importance during the pulse phase $T_3$ in the course of which the measuring capacitor $C_M$ is charged.

In the reflections following hereinbelow, a square-wave current is generally taken as a basis, said square-wave current flowing through the arrangements from A to D or vice versa for respective identical periods of time. As can be seen in FIG. 3, the current is produced by a direct-current source SQ whose polarity is periodically reversed with the aid of controlled switches S1 to S4.

The process described is subdivided into two subprocesses for explanatory reasons, viz., on the one hand, the explanation of the processes in connection with the impression of the measuring current and, on the other hand, the measurement of a voltage which is proportional to the specific resistance of the electrolyte.

Figure 6A:
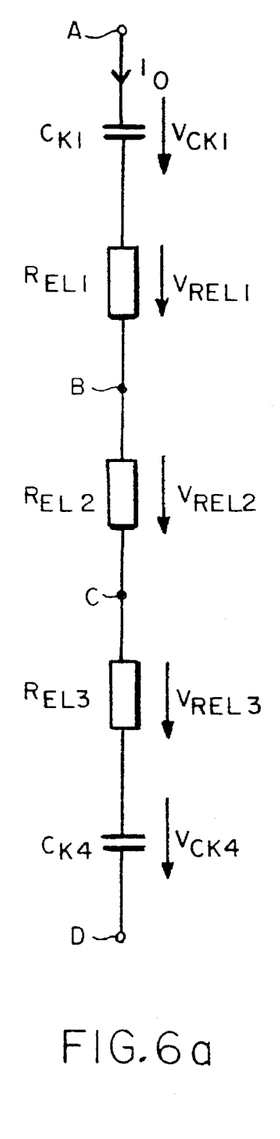
FIG. 6a shows the effective electric equivalent circuit diagram of the arrangement of the coupling capacitors upon impression of the measuring current.
Figure 6B:
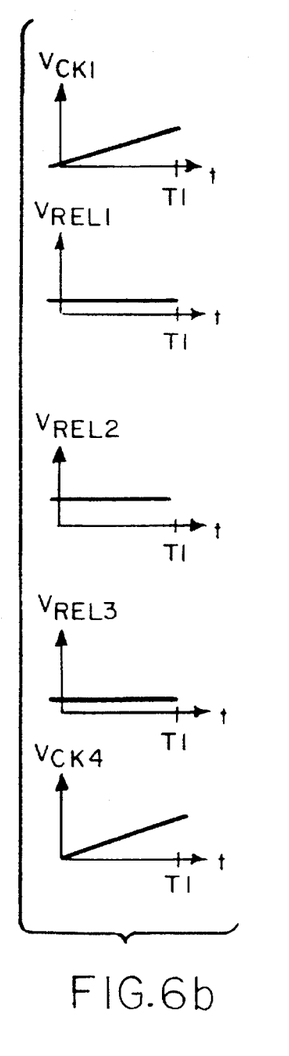
FIG. 6b is a collection of waveforms depicting corresponding voltage drops across the elements of the equivalent circuit diagram of FIG. 6a, as a function of time.
Figure 6C:
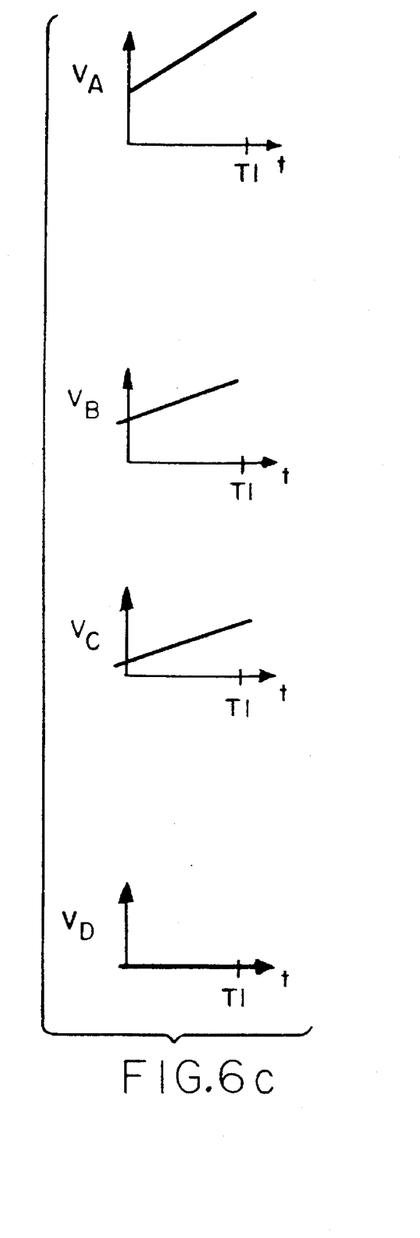

FIG. 6a shows the effective electric equivalent circuit diagram for the impression of the measuring current. In order to make things easier, only the flow of current in a direction from A to D (pulse phase $T_1$) is examined in the present connection, since a flow of current in the opposite direction (pulse phase $T_2$) will only have the effect that the signs change. Point D is assumed to be connected to ground for the period of time taken into consideration. The constant current will then cause a linear rise in the voltage at the capacitor $C_{K4}$ in accordance with the following equation:

$$V_{CK4} = \frac{I_0 t}{C_{K4}} \tag{1}$$

The element of the electric equivalent circuit diagram following the fourth coupling capacitor $C_{K4}$, viz. the third ohmic electrolyte resistor $R_{EL3}$, causes a constant voltage drop due to the measuring current in accordance with the following equation:

$$V_{REl3} = I_0 R_{El3} \tag{2}$$

Also the other two ohmic divider resistors $R_{El2}$, $R_{El1}$ cause the following voltage drops:

$$V_{REl2} = I_0 R_{El2} \tag{3}$$

$$V_{REl1} = I_0 R_{El1} \tag{4}$$

The voltage at point C is obtained in accordance with the equation following hereinbelow as sum of the voltages across the fourth coupling capacitor $C_{K4}$ and the third electrolyte resistor $R_{El3}$:

$$V_C = V_{CK4} + V_{REl3} = \frac{I_0 t}{C_{K4}} + I_0 R_{El3} \tag{5}$$

Accordingly, the following equation is obtained for the voltage at point B:

$$V_B = V_{CK4} + V_{REl3} + V_{REl2} = \frac{I_0 t}{C_{K4}} + I_0 R_{El3} + I_0 R_{El2} \tag{6}$$

The upper capacitor $C_{K1}$ has the same size and the same structural design as the capacitor $C_{K4}$ and causes a voltage drop which corresponds to that caused by said capacitor $C_{K4}$ and which satisfies the following equation:

$$V_{CK1} = \frac{I_0 t}{C_{K1}} \tag{7}$$

With regard to the further evaluation, it is now of decisive importance that, although the voltages at points B and C are absolutely rampshaped, the difference between them is constant and depends only on the measuring current and the electrolyte resistance. Hence, the following equation holds true:

$$V_B - V_C = I_0 R_{El2}$$

For detecting this differential voltage, two additional coupling capacitors $C_{K2}$ and $C_{K4}$ are used, which are arranged between the above described capacitors $C_{K1}$ and $C_{K4}$. During a time $T_3$ after the change of polarity of the measuring current, i.e. when stationary conditions occurred with respect to the ohmic voltage drop across the electrolyte, these coupling capacitors $C_{K2}$ and $C_{K4}$ are connected to the measuring capacitor $C_M$ via the switches $S_5$ and $S_6$. An analogous course of action is taken when the current flows in the opposite direction. In this case, the switches $S_7$ and $S_8$ are used in a corresponding manner during the period of time $T_4$ within the period of time $T_2$.

For analyzing the process, the ohmic voltage drop across the divider electrolyte resistor $R_{El2}$ is shown in FIG. 4 as a voltage source. This is admissible, although the original distribution of current is interfered with due to the fact that the branch including the measuring capacitor $C_M$ is charged, since this branch becomes current-free again after a short period of time so that, afterwards, the conditions will be the same as if no measuring capacitor $C_M$ were provided.

The following boundary conditions apply to the charging process of $C_M$:

the charging takes place exponentially, since only resistors and capacitors are located in the circuit in question.

The time constant is defined by the dual switch-on resistance of the CMOS switches as well as by the series connection of the coupling capacitors $C_{K2}$, $C_{K3}$ and the measuring capacitor $C_M$. $C_{K2}$ corresponds to $C_{K3}$ in this case. The charging time constant can be expressed by the following equation:

$$t_M = 2 R_{ON} \frac{C_M C_{K2}}{(C_{K2} + 2C_M)} \quad (9)$$

The time constant $t_M$ obtained with the realized circuit lies within the range of a few 10 ns so that charging of the measuring capacitor $C_M$ within a very short time, in comparison with the duration of the voltage ramp of some 10 Is, is guaranteed. The final value of the voltage across the measuring capacitor $C_M$ is obtained from the capacitive division ratio of the existing capacitors in accordance with the following equation:

$$V_{CMEnd} = I_0 R_{E12} \frac{C_{K2}}{(C_{K2} + 2C_M)} \quad (10)$$

Having obtained this voltage $V_{CMEnd}$, a measuring signal which is proportional to the electrolyte resistance $R_{E12}$ is now available. Due to the given geometrical conditions of the measuring arrangement, the second electrolyte divider resistor $R_{E12}$ is linked via a constant with the specific resistance and by the formation of a reciprocal with the conductivity of the electrolyte. This constant can quasi be regarded as a "cell constant" of the arrangement.

Figure 7A:
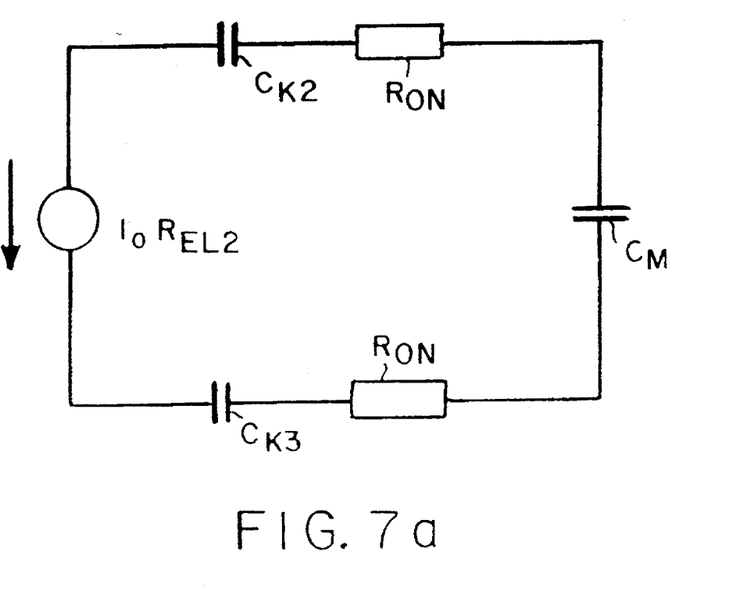
FIG. 7a shows the effective electric equivalent circuit diagram of the arrangement of the coupling capacitors according to FIG. 5a upon measurement of the signal voltage.
Figure 7B:
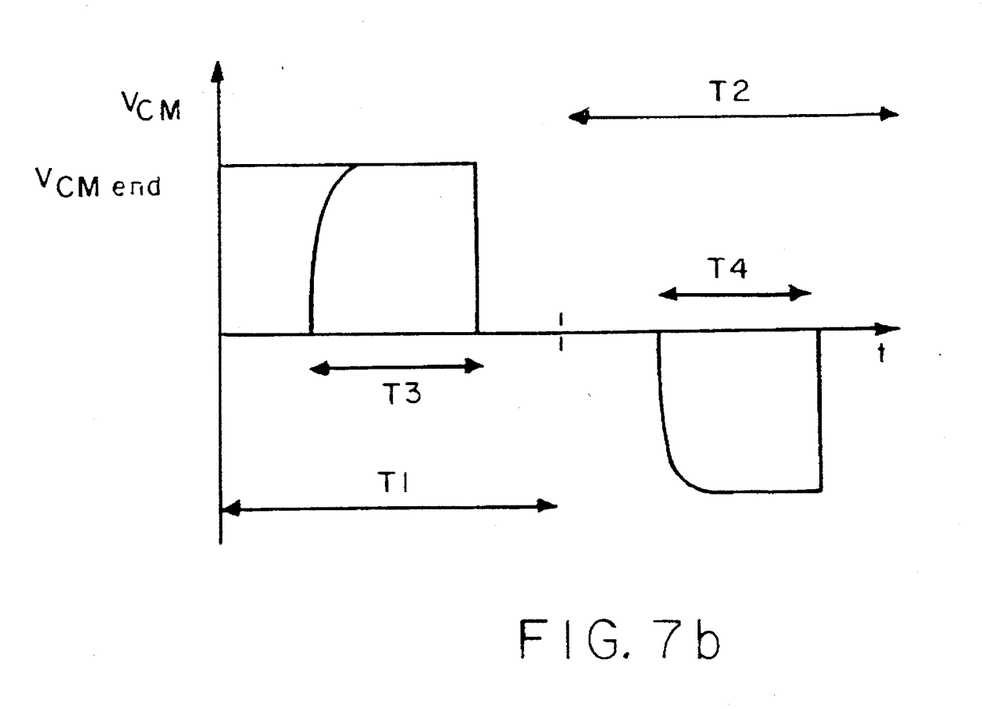
FIG. 7b shows the variations with time of the voltages across the measuring capacitor of the conductivity measuring device according to FIG. 4.

The variations with time of the voltage across the measuring capacitor $C_M$ are shown in FIG. 7b.

When the measuring signal has been transmitted to the measuring capacitor $C_M$, the switches $S_5$ and $S_6$ are reopened, the charge on the measuring capacitor $C_M$ being maintained in the course of this process (cf. FIG. 7a). For the purpose of further processing, said charge is introduced into the switch-capacitor circuit according to FIG. 3 by means of additional switches $S_9$ and $S_{10}$ and then amplified. In the course of this process, the charge stored on the measuring capacitor $C_M$ is transferred to the feedback capacitor $C_R$, the capacitance ratio of $C_M$ to $C_R$ defining the amplification factor. The output voltage $V_{OUT}$ is available as an output value after each charging process. If the operational amplifier is connected as an integrator in the case of which the voltage across the feedback capacitor $C_R$ is only reset after several cycles by the eleventh switch $S_{11}$, it will be possible to amplify the output signal still further.

The conductivity measuring device according to the present invention excludes polarization effects, it prevents electrolysis processes in the electrolyte, and it also excludes or markedly reduces drift errors caused by an absorption of ions or by contamination in the area of the measuring elements. The electrolyte is not at a fixed potential, whereby the range of application of the conductivity measuring device according to the present invention is enlarged still further. In view of the fact the electrolyte need not be in contact with metals, undesired chemical reactions, such as catalytic reactions, are avoided.

We claim:

1. An integrable conductivity measuring device for measuring the electric conductivity of liquids, comprising a current source device adapted to be connected to two current supply elements through which a substantially square-wave current can be fed into the liquid, and a measuring circuit connected to two voltage measuring elements and used for determining the voltage drop in the liquid between said voltage measuring elements, said voltage drop depending on the electric conductivity of the liquid examined, said voltage measuring elements comprising voltage decoupling capacitors, wherein the measuring circuit is a switch-capacitor circuit including a measuring capacitor, a differential amplifier having a feedback capacitor arranged in its feedback branch, and a switch means with the aid of which the two connections of the measuring capacitor are connected in time dependence on the behaviour of the square-wave current to the voltage electrodes in one switching state and to the two inputs of the differential amplifier in another switching state, and the current supply elements are implemented as current coupling capacitors.

2. An integrable conductivity measuring device according to claim 1, wherein each coupling and decoupling capacitor is formed as a conductive layer on an insulating intermediate layer, which, in turn, is positioned on a semiconductor substrate, and is covered by an insulating surface layer.

3. An integrable conductivity measuring device according to claim 2, wherein the insulating surface layer consists of silicon oxide and silicon nitride, the conductive layer consists of polysilicon, and the insulating intermediate layer consists of silicon oxide.

4. An integrable conductivity measuring device according to claim 1, wherein the current source device comprises a direct-current source which is adapted to be connected via first, second, third and fourth switches to the current coupling capacitors in a first and in a second polarity.

5. An integrable conductivity measuring device according to claim 1, comprising a control device, which controls the first, second, third and fourth switches in such a way that they connect the current source to the current coupling capacitors alternately during a first period of time in the first polarity and during a second period of time in the second polarity.

6. An integrable conductivity measuring device according to claim 5, wherein the switch means has fifth, sixth, seventh and eighth switches, the control device controls the fith to eighth switches in such a way that they connect the voltage decoupling capacitors to the measuring capacitor during a third period of time in a first polarity and during a fourth period of time in a second polarity, and the third period of time lies within the first period of time and the fourth period of time within the second period of time.

7. An integrable conductivity measuring device according to claim 5, wherein the first and second periods of time are of equal length so that the square-wave current has no dc component averaged over time.

8. An integrable conductivity measuring device according to claim 1, wherein the measuring circuit is provided with an amplifier circuit which is adapted to be connected to the measuring capacitor via ninth and tenth switches.

9. An integrable conductivity measuring device according to claim 2, wherein the control device controls said ninth and tenth switches in such a way that they connect the amplifier circuit to the measuring capacitor during a fifth period of time, which does not lie within said third and fourth periods of time.

10. An integrable conductivity measuring device according to claim 8, wherein the measuring circuit is provided with feedback capacitor located in the feedback branch of the amplifier circuit.

11. An integrable conductivity measuring device according to claim 10, comprising an eleventh switch connected in parallel to the feedback capacitor, wherein the control device controls the eleventh switch in such a way that the feedback capacitor is discharged after each fifth period of time.

12. An integrable conductivity measuring device according to claim 10, comprising an eleventh switch connected in parallel to the feedback capacitor, wherein the control device controls the eleventh switch in such a way that the feedback capacitor is discharged whenever a plurality of periods has elapsed.

* * * * *